United States Patent
Po et al.

(10) Patent No.: US 10,691,998 B2
(45) Date of Patent: Jun. 23, 2020

(54) GENERATING TEMPLATED DOCUMENTS USING MACHINE LEARNING TECHNIQUES

(71) Applicant: Google Inc., Mountain View, CA (US)

(72) Inventors: Ming Jack Po, Mountain View, CA (US); Christopher Co, Saratoga, CA (US); Katherine Chou, Palo Alto, CA (US)

(73) Assignee: Google LLC, Mountain View, CA (US)

(*) Notice: Subject to any disclaimer, the term of this patent is extended or adjusted under 35 U.S.C. 154(b) by 531 days.

(21) Appl. No.: 15/385,804

(22) Filed: Dec. 20, 2016

(65) Prior Publication Data

US 2018/0174043 A1    Jun. 21, 2018

(51) Int. Cl.
*G06N 3/08*     (2006.01)
*G06N 5/02*     (2006.01)
*G16H 50/20*    (2018.01)
*G06Q 50/22*    (2018.01)

(52) U.S. Cl.
CPC ............. *G06N 3/08* (2013.01); *G06N 5/022* (2013.01); *G06Q 50/22* (2013.01); *G16H 50/20* (2018.01)

(58) Field of Classification Search
CPC .......... G06N 3/08; G06N 5/022; G16H 50/20; G06Q 50/22
See application file for complete search history.

(56) References Cited

U.S. PATENT DOCUMENTS

| | | |
|---|---|---|
| 2014/0279746 A1 | 9/2014 | De Bruin et al. |
| 2015/0257712 A1 | 9/2015 | Sarrafzadeh et al. |
| 2016/0328526 A1 | 11/2016 | Park et al. |
| 2019/0034416 A1* | 1/2019 | Al Hasan ............ G06F 17/2785 |

OTHER PUBLICATIONS

Lipton et al, Learning to diagnose with LSTM recurrent neural networks, Nov. 11, 2015, arxiv (Year: 2015).*
International Preliminary Report on Patentability for Application No. PCT/US2017/054484, dated Mar. 18, 2019, 22 pages.
International Search Report for PCT/US2017/054484 dated Dec. 20, 2017, 10 pages.
Google AI Blog, "Computer, Respond to This Email.", Nov. 3, 2015, https://ai.googleblog.com/2015/11/computer-respond-to-this-email.html, retrieved on Dec. 16, 2019, 4 pages.

* cited by examiner

*Primary Examiner* — Austin Hicks
(74) *Attorney, Agent, or Firm* — Dority & Manning, P.A.

(57) ABSTRACT

Systems and methods of predicting documentation associated with an encounter between attendees are provided. For instance, attendee data indicative of one or more previous visit notes associated with a first attendee can be obtained. The attendee data can be inputted into a machine-learned note prediction model that includes a neural network. The neural network can generate one or more context vectors descriptive of the attendee data. Data indicative of a predicted visit note can be received as output of the machine-learned note prediction model based at least in part on the context vectors. The predicted visit note can include a set of predicted information expected to be included in a subsequently generated visit note associated with the first attendee.

14 Claims, 4 Drawing Sheets

GENERATING TEMPLATED DOCUMENTS USING MACHINE LEARNING TECHNIQUES

FIELD

The present disclosure relates generally to machine-learned models for predicting documentation of encounters between attendees.

BACKGROUND

Attendees at meetings or other encounters often generate records or notes that document the meetings. Such records or notes can include information relating to the information discussed in the meetings and/or information to be associated with future meetings. For instance, doctors generally document doctor-patient encounters between the doctor and a patient by generating a visit note associated with the doctor-patient encounter. Such visit note can include information relating to a medical history of the patient, discussions between the doctor and the patient during the DPE (e.g. health problems or symptoms reported by the patient), the doctor's findings (e.g. physical exam results), the doctor's diagnosis, a proposed treatment plan, rationale for the treatment plan, the doctor's analysis, care arrangements for the patient, medical needs of the patient, non-medical needs of the patient, follow up procedures or plans (e.g. additional tests or studies, follow up appointments, referrals to a specialist, etc.), and/or any other suitable information relating to the DPE or to the patient in general.

Generating such notes can consume significant time and resources. Further, notes that are generated manually (e.g. typed, handwritten, etc.) can include errors. As an example, visit notes generated by a doctor that include such errors can lead to clinical errors that can endanger patient safety. Various tools and techniques have been introduced to aid in generating such notes, and to increase the accuracy with which the notes are recorded. Such conventional techniques for visit note aid include providing templates that can be used to generate suitable notes. Further techniques include auto-populating information to be included in a visit note. However, such auto-population techniques can be inaccurate, and/or inefficient.

SUMMARY

Aspects and advantages of embodiments of the present disclosure will be set forth in part in the following description, or may be learned from the description, or may be learned through practice of the embodiments.

One example aspect of the present disclosure is directed to a computer-implemented method of predicting documentation associated with an encounter between attendees. The method includes obtaining, by one or more computing devices, attendee data indicative of one or more previously generated visit notes associated with a first attendee of an encounter. The method further includes inputting, by the one or more computing devices, the attendee data into a machine-learned note prediction model comprising a neural network. The method further includes receiving as output of the machine-learned note prediction model, by the one or more computing devices, data indicative of a predicted visit note, the predicted visit note comprising a set of predicted information expected to be included in a subsequently generated visit note associated with the first attendee.

Other example aspects of the present disclosure are directed to systems, apparatus, tangible, non-transitory computer-readable media, user interfaces, memory devices, and electronic devices for predicting visit notes.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
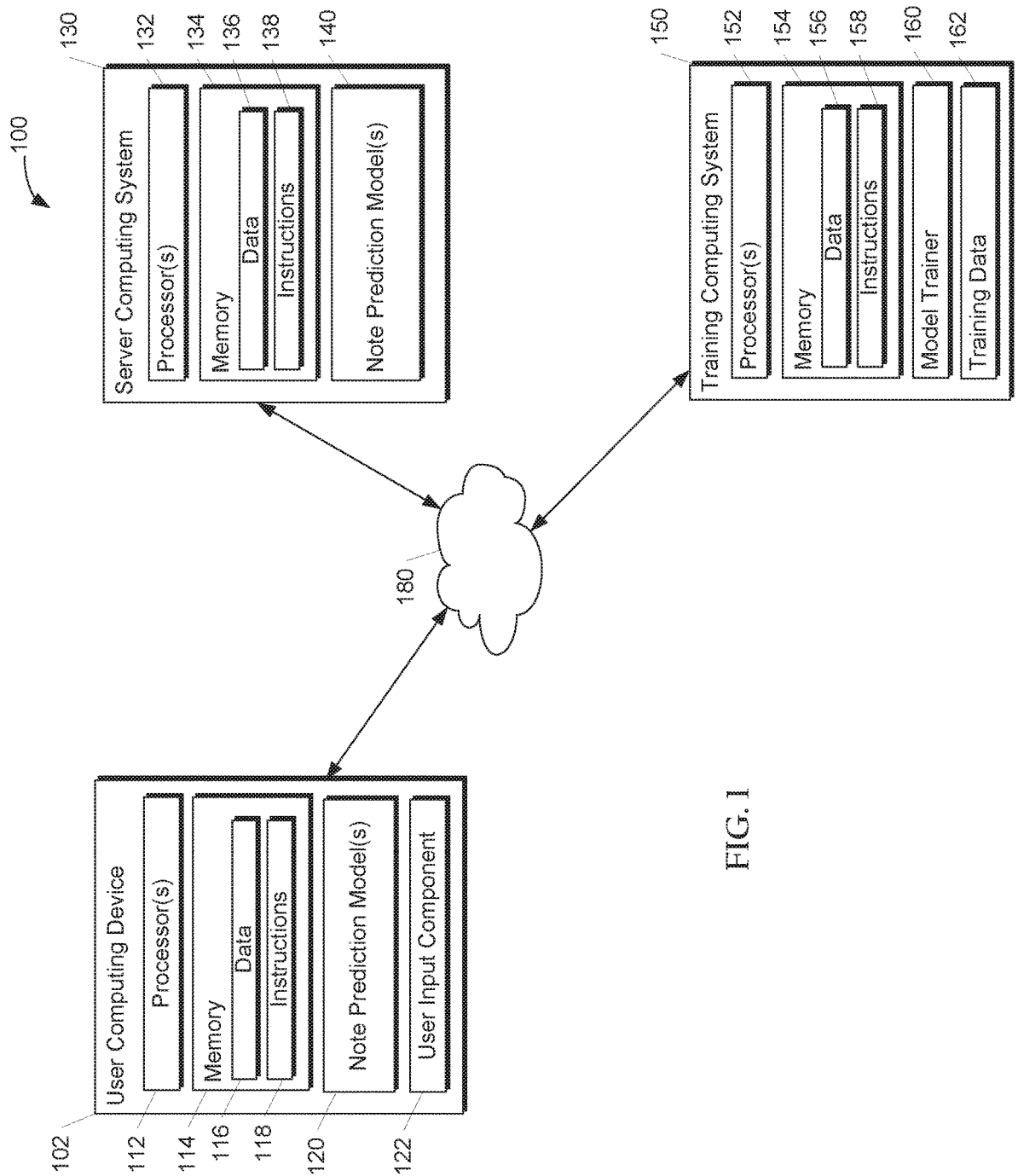
FIG. 1 depicts an example system according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to machine-learned models configured to generate predicted documentation associated with an encounter (e.g. meeting, appointment, interview, etc.) between two or more attendees. Such machine-learned models can be used to generate predicted visit notes relating to encounters between attendees. As used herein, the term "visit note" can refer to any suitable documentation relating to an encounter between attendees. As an example, an encounter can be a doctor's appointment, and attendees of the encounter can include a doctor and a patient. Doctors generally generate visit notes subsequent to a doctor-patient encounter (DPE), such as an appointment, check-up, physical, etc. A visit note can document information relating to the patient and/or the DPE. For instance, the visit note can document information such as a medical history of the patient, discussions between the doctor and the patient during the DPE (e.g. health problems or symptoms reported by the patient), the doctor's findings (e.g. physical exam results), the doctor's diagnosis, a proposed treatment plan, rationale for the treatment plan, the doctor's analysis, care arrangements for the patient, medical needs of the patient, non-medical needs of the patient, follow up procedures or plans (e.g. additional tests or studies, follow up appointments, referrals to a specialist, etc.), and/or any other suitable information relating to the DPE or to the patient in general. Such visit notes may be generated by the doctor as a matter of course subsequent to a DPE and included in the medical records of the patient.

In this manner, example aspects of the present disclosure provide systems and methods that leverage machine learning to generate automated predicted visit notes associated with an encounter between a first attendee (e.g. patient) and a second attendee (e.g. doctor). Although the present disclosure is discussed with respect to generating predicted visit notes associated with DPEs, it will be appreciated that example aspects of the present disclosure can be used in any suitable templating application. For instance, the machine-learned models of the present disclosure can be trained to generate any suitable form of predicted text output associated with any suitable encounter. In this manner, aspects of the present disclosure can be used to generate predicted documentation of encounters between attorneys and clients, employers and employees, social workers and clients, interviewer and interviewee, and/or any other suitable encounter between two or more people.

More particularly, the systems and methods of the present disclosure can include and use a machine-learned note prediction model that is trained to receive information associated with a first attendee associated with a subject encounter between the first attendee (e.g. patient) and a second attendee (e.g. doctor), and to generate a predicted text output documenting the encounter based at least in part on the information associated with the first attendee. The predicted text output can include predicted information that is expected to be included in a suitable document describing the encounter. In this manner, attendee data associated with the first attendee can be obtained. For instance, in implementations wherein the encounter is a DPE between a doctor and a patient, the attendee data can include patient data associated with the patient. The patient data can include any suitable patient data. For instance, such patient data can be indicative of one or more previous visit notes respectively associated with one or more previous DPEs of the patient. As another example, the patient data can include any suitable structured or unstructured data associated with a medical history or record of the patient. As another example, the patient data can include data obtained from one or more ambient and/or consumer sensors. For instance, such patient data can include data obtained from a biometric sensor (e.g. heart rate data or other data) associated with a wearable computing device associated with the patient.

The patient data can be received subsequent to a provision of consent from the patient allowing the use of such patient data. In this manner, example aspects of the present disclosure can be performed contingent on receiving such patient consent. In some implementations, the patient data can be treated in one or more ways before or after it is used so that personally identifiable information is removed or not stored permanently.

In response to receiving the patient data, the note prediction model can output a predicted visit note associated with the patient. For instance, the predicted visit note can be associated with a subject DPE between the doctor and the patient. A subject DPE can be a DPE occurring between the doctor and the patient for which a visit note has not yet been generated. The predicted visit note can include information that is expected to be included in a subsequent visit note associated with a DPE between the doctor and the patient that is generated by the doctor.

More particularly, the machine-learned note prediction model can include one or more neural networks (e.g. deep neural networks). The neural networks can be recurrent neural networks, such as long short-term memory (LSTM) neural networks, gated recurrent unit (GRU) neural networks, or other forms of neural networks. In one example a computing device can obtain patient data that describes one or more previous visit notes associated with the patients. In some implementations, the computing device can further obtain patient data relating to a subject DPE. The patient data relating to the subject DPE can be associated with information input by the doctor (or other person) relating to the subject DPE. More particularly, the patient data relating to the subject DPE can be associated with information that has not yet been recorded in a visit note. The computing device can input the patient data (e.g. the patient data indicative of the one or more previous notes and/or the patient data relating to the subject DPE) into the note prediction model, and can receive a predicted note as output of the note prediction model.

As indicated, the predicted visit note generated by the note prediction model can include predicted information expected to be included in a subsequent visit note associated with the patient. The predicted visit note can include substantive information determined by the note prediction model. For instance, such substantive information can include information not included in the patient data. Such predicted information can be determined based at least in part on the patient data associated with the patient. Such predicted information can further be determined based at least in part on one or more previous visit notes generated by the doctor (e.g. for any suitable number of patients), and/or one or more previous visit notes generated by various other suitable doctors for various other suitable patients.

For instance, such predicted information can include information relating to a medical history of the patient, symptoms or health problems reported by the patient or expected to be reported by the patient, a predicted diagnosis, a predicted treatment plan, a rationale for the predicted treatment plan, predicted analysis, predicted care arrangements for the patient, predicted medical needs of the patient, predicted non-medical needs of the patient, predicted follow up procedures or plans, and/or other suitable predicted information relating to the subject DPE or the patient in general. In this manner, the predicted visit note can include information learned by the note prediction model based at least in part on the patient data, one or more previous visit notes generated by the doctor (e.g. for any suitable number of patients), one or more previous visit notes generated by various other suitable doctors for various other suitable patients, and/or other suitable structured or unstructured data associated with the patient, one or more other patients, and/or the doctor. In implementations wherein the predicted visit note is determined based at least in part on patient data input by the doctor associated with the subject DPE, the predicted note can include information associated with such input patient data. For instance, if such patient data includes a list of symptoms provided by the patient (e.g. during the subject DPE or prior to the subject DPE, such as during a telephone call to schedule an appointment with the doctor), the predicted note can include the list of symptoms. In such implementations, the predicted information (e.g. predicted diagnosis, treatment plan, etc.) can be determined based at least in part on the symptoms provided by the patient.

The predicted visit note can be generated such that the information included in the predicted note is provided in a grammatically and/or syntactically correct form. For instance, the note prediction model can be configured to generate words, phrases, sentences, paragraphs, passages, etc. that collectively provide a coherent, easily understandable, grammatically correct visit note that can be analyzed by the doctor. For instance, in some implementations, the predicted note can be synthesized by the note prediction model on a word-by-word basis to construct grammatically correct sentence structures that provide the predicted information for a subsequent visit note.

In some implementations, the predicted visit note can be determined based at least in part on one or more previous visit notes generated by the doctor. More particularly, the predicted visit note can be generated such that the information provided in the predicted note is provided in a format and/or style determined based at least in part on the previous visit notes generated by the doctor. For instance, the predicted visit note can have a format (e.g. arrangement or configuration of information included in the predicted note), style (e.g. writing style, such as vocabularies, sentence structure, paragraph structure, etc.) context, etc. that mimics or emulates that of one or more previous visit notes generated by the doctor. In this manner, the predicted notes can be tailored to a particular format, stylization, etc. previously used by the doctor.

As indicated, the note prediction model can include one or more neural networks (e.g. feed-forward neural networks, recurrent neural networks). In some implementations, the note prediction model can include two phases. Each phase can include a neural network. In particular, in a first phase, a computing device can input a set of patient data and/or other input data to a first neural network (e.g. LSTM network). In response to receipt of the patient data, the first neural network can output a context vector. The context vector can specify information included in the patient data. For instance, the context vector can be grammar agnostic, such that the context vector captures a general gist of the information included in the patient data, without regard to grammar or stylization of the information.

In a second phase of the note prediction model, the context vector can be into a second neural network (e.g. LSTM network). The second neural network can output a predicted visit note associated with the patient in accordance with example aspects of the present disclosure.

In some implementations, the second neural network can be configured to output a plurality of note prediction vectors. The note prediction vectors can describe information to potentially be included in a subsequent visit note. The note prediction vectors can be provided to a suggestion model configured to provide visit note suggestions to the doctor (or other person) as the doctor (or other person) is generating the visit note. The suggestion model can be a machine-learned model that includes one or more hidden Markov models, support vector machines, neural networks (e.g., feed-forward neural networks, recurrent neural networks such as LSTM recurrent neural networks), phrase-based translators, sequence-to-sequence models, or other suitable models. For instance, the doctor can input a first text entry into a suitable user interface. The first text entry can be provided as input to the suggestion model along with the note prediction vectors, and the suggestion model can provide as output one or more suggested text entries for completing the text entry. The doctor can then select one or more of the suggested text entries to complete the text entry. In this manner, the completed text entry can include information associated with the first text entry provided by the user and the selected suggested text entry provided by the suggestion model.

The machine-learned models described herein can be trained using suitable training data, such as for instance, a global set of visit notes generated by a plurality of doctors of a plurality of patients, and a set of doctor specific visit notes previously generated by the doctor. More particularly, a training computing system can train the note prediction models using a training dataset that includes a number of global visit notes and a number of doctor specific visit notes.

In some implementations, to train the note prediction model, a first subset of a set of training data (e.g. data indicative of one or more global visit notes and/or one or more doctor specific visit notes) is input into the motion prediction model to be trained. In response to receipt of such first portion, the motion prediction model outputs a predicted note that predicts a subsequent visit note based at least in part on the first subset of training data. After such prediction, the training computing system can apply or otherwise determine a loss function that compares the predicted visit note output by the note prediction model to an actual subsequent visit note of the training data that the note prediction model attempted to predict. In some implementations, the training computing system can backpropagate (e.g., by performing truncated backpropagation through time) the loss function through the note prediction model. In some implementations, the training computing system can determine the loss function for a whole mini-batch of training data at once.

In some implementations, in order to obtain the benefits of the techniques described herein, users (e.g. encounter attendees, such as patients, doctors, clients, employees, employers, etc.) may be required to allow the periodic collection and analysis of visit notes describing one or more encounters associated with the user. Therefore, users can be provided with an opportunity to give consent as to whether and how much the systems and methods of the present disclosure collect and/or analyze such information. However, if the user does not allow collection and use of such information, then the user may not receive the benefits of the techniques described herein. In addition, in some embodiments, certain information or data can be treated in one or more ways before or after it is used, so that personally identifiable information is removed or not stored permanently.

With reference now to the figures, example aspects of the present disclosure will be discussed in greater detail. For instance, FIG. 1 depicts an example system 100 for predicting visit notes according to example aspects of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, a FPGA, a controller, a microcontroller, etc.) and can be one processor or a plurality of processors that are operatively connected. The memory 114 can include one or more non-transitory computer-readable storage mediums, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

The user computing device 102 can store or include one or more note prediction models 120. For example, the note prediction models 120 can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, or other forms of neural networks. Example note prediction models 120 are discussed with reference to FIGS. 2 and 3.

In some implementations, the one or more note prediction models 120 can be received from the server computing system 130 over network 180, stored in the user computing device memory 114, and the used or otherwise implemented by the one or more processors 112. In some implementations, the user computing device 102 can implement multiple parallel instances of a single note prediction model 120.

More particularly, the note prediction model(s) 120 can be used in templating a predicted visit note associated with a patient and/or a doctor. For instance, the predicted visit note can be associated with a subject DPE between the doctor and the patient. The subject DPE can be an upcoming DPE (e.g. a scheduled DPE) or a DPE that has already occurred. In this manner, the note prediction model(s) 120 can generate the predicted visit note for review by the doctor or other person. The note prediction model(s) 120 can be trained to determine a predicted visit note for a patient. More particularly, the user computing device 102 can provide patient data as input to the note prediction model(s) 120, and the not prediction model(s) 120 can provide a predicted visit note as output based at least in part on the patient data. The patient data can include data indicative of one or more previous visit notes associated with one or more previous DPEs between the patient and one or more doctors. The patient data can further include data associated with the subject DPE. For instance, such data can include any suitable data associated with the patient recorded in association with the subject DPE (either prior to the subject DPE or subsequent to the subject DPE). Such data can be input to the user computing device 102 or other computing device by any suitable user.

The note prediction model(s) 120 can be employed within various suitable applications associated with the user computing device 102. For instance, the note prediction model(s) 120 can be employed within the context of a suitable application associated with the templating of visit notes. As another example, the note prediction model(s) 120 can be included as a browser plug-in or web-based application associated with the user device 102.

Additionally or alternatively, one or more note prediction models 140 can be included in or otherwise stored and implemented by the server computing system 130 that communicates with the user computing device 102 according to a client-server relationship. For example, the note prediction models 140 can be implemented by the server computing system 140 as a portion of a web service (e.g., a visit note templating service). Thus, one or more models 120 can be stored and implemented at the user computing device 102 and/or one or more models 140 can be stored and implemented at the server computing system 130.

The user computing device 102 can also include one or more user input component 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone suitable for voice recognition, a traditional keyboard, mouse or other means by which a user can enter a communication.

The server computing system 130 includes one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage mediums, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise includes one or more machine-learned note prediction models 140. For example, the note prediction model(s) 140 can be or can otherwise include various machine-learned models such as neural networks (e.g., deep recurrent neural networks) or other multi-layer non-linear models. Example communication assistance models 140 are discussed with reference to FIGS. 2 and 3.

The server computing system 130 can train the communication assistance models 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, a FPGA, a controller, a microcontroller, etc.) and can be one processor or a plurality of processors that are operatively connected. The memory 154 can include one or more non-transitory computer-readable storage mediums, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 140 stored at the server computing system 130 using various training or learning techniques, such as, for example, backwards propagation of errors. In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train a note prediction model 140 based on a set of training data 142. The training data 142 can include, for example, data indicative of a plurality of global visit notes associated with a plurality of DPEs between a plurality of doctors and a plurality of patients. The training data 142 can further include a plurality of doctor specific visit notes generated by the doctor associated with a plurality of DPEs between the doctor and a plurality of patients. In some implementations, the global visit notes can be grouped according to patient, doctor, or other suitable grouping metric associated with the respective visit notes. For instance, a group of global visit notes can be grouped in a sequence according to a chronology of DPEs associated with a patient. Similarly, the doctor specific notes can be grouped according to patient or other suitable grouping metrics in accordance with a chronology of DPEs.

In some implementations, if the user has provided consent, the training examples can be provided by the user computing device 102 (e.g., based on visit notes previously provided by the user of the user computing device 102). Thus, in such implementations, the model 120 provided to the user computing device 102 can be trained by the training computing system 150 on user-specific communication data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM hard disk or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 1 illustrates one example computing system that can be used to implement the present disclosure. Other computing systems can be used as well. For example, in some implementations, the user computing device 102 can include the model trainer 160 and the training dataset 162. In such implementations, the communication assistance models 120 can be both trained and used locally at the user computing device 102. In some of such implementations, the user computing device 102 can implement the model trainer 160 to personalize the communication assistance models 120 based on user-specific data.

Figure 2:
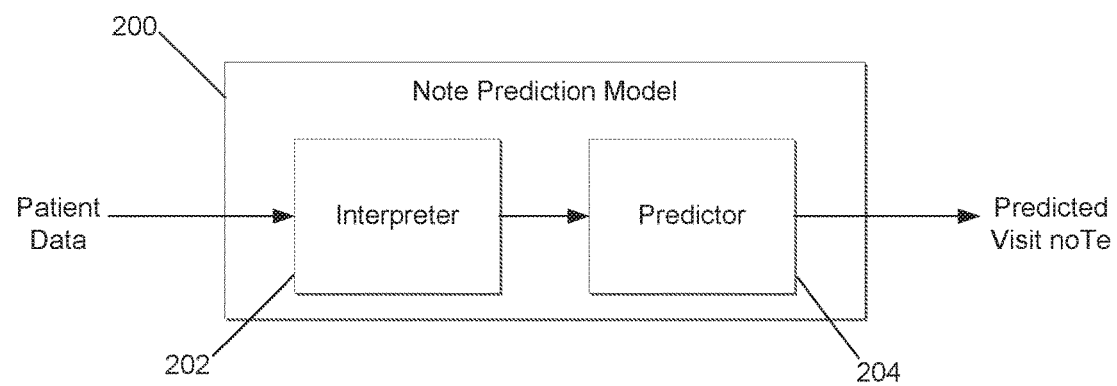
FIGS. 2-3 depict example machine-learned note prediction models according to example embodiments of the present disclosure.

FIG. 2 depicts a block diagram of an example note prediction model 200 according to example embodiments of the present disclosure. In some implementations, the note prediction model 200 can be configured to receive a set of patient data descriptive of one or more visit notes generated for one or more previous DPEs and/or information associated with a subject DPE associated with a patient. The note prediction model can be trained to output one or more predicted visit notes in response to the receipt of the patient data. In some implementations, the set of patient data can be a set of sequential patient data. For instance, the sequential patient data can describe visit notes in an order in which they were generated (e.g. corresponding to a chronological order of the DPEs).

The note prediction model 200 includes an interpreter 202 and a predictor 204. The interpreter 202 can include one or more neural networks (e.g. deep neural networks). For instance, the interpreter 202 can include one or more recurrent neural networks, such as for instance, LSTM recurrent neural networks, gated recurrent unit networks, or other suitable networks. In other implementations, in addition or alternatively to one or more neural networks, the interpreter 202 of the note prediction model 200 can include other forms of machine-learned models such as, for example, support vector machines, hidden Markov models, and other machine-learned classifiers. In addition, in some implementations, the interpreter 202 can include or implement additional alternative approaches such as rule-based systems (e.g., as machine-learned from data or manually created).

The one or more neural networks or other machine-learned models of the interpreter 202 can be trained on a training dataset that includes, for example, training visit notes (e.g. global visit notes and/or doctor specific visit notes). The training dataset can include any suitable structured or unstructured data or information relating to the medical history or record of the user. In some implementations, the training data can include data obtained from one or more ambient and/or consumer sensors. For instance, such training data can include data obtained from a biometric sensor associated with a wearable computing device associated with the patient. As indicated, in some implementations, such training data can be received contingent upon receiving consent from the respective patients with which the training data are associated. In this manner, such patients can be provided with opportunities to control whether such data is collected and/or the manner in which the data is analyzed. As indicated, the training data can include a sequential set of visit notes ordered chronologically according to DPE. In some implementations the training data can be grouped by doctor and/or by patient. For instance, a subset of training data can include data indicative of a plurality of chronologically ordered visit notes generated for a patient (e.g. by one or more doctors) in response to a plurality of DPEs. As another example, a subset of training data can include data indicative of a plurality of (e.g. chronologically ordered) visit notes generated by a particular doctor.

In this manner, the interpreter 202 can be trained to recognize and/or interpret information included within patient data (e.g. visit notes or other suitable communications) for a patient. For instance, the interpreter 202 can be trained to output one or more context vectors descriptive of one or more input visit notes provided as input to the interpreter 202. The context vectors can specify information included within the visit notes and/or other patient data. In some implementations, the context vectors can specify such information in a grammar and/or formatting agnostic manner. A context vector can provide a general gist of information included in at least a portion of one or more visit notes.

The note prediction model 200 can further include predictor 204. The predictor 204 can include one or more neural networks (e.g. deep neural networks). For instance, the predictor 204 can include one or more recurrent neural networks, such as for instance, LSTM recurrent neural networks, gated recurrent unit networks, or other suitable networks. In other implementations, in addition or alternatively to one or more neural networks, the interpreter 242 of the note prediction model 200 can include other forms of machine-learned models such as, for example, support vector machines, hidden Markov models, and other machine-learned classifiers. In addition, in some implementations, the interpreter 202 can include or implement additional alternative approaches such as rule-based systems (e.g., as machine-learned from data or manually created).

The output of the interpreter 202 can be provided to the predictor 204. The one or more neural networks or other machine-learned models of the predictor 204 can be trained on a suitable training data set according to example aspects of the present disclosure. For instance, the training data set can be the same data set or a similar data set as the data set used to train the interpreter 202. In this manner, the training data set can include data indicative of one or more global visit notes and/or one or more doctor specific visit notes.

The predictor 204 can be trained to output one or more predicted visit notes as a result of receiving the context vectors or other output of the interpreter 202. In this manner, the predictor 204 can output a predicted visit note based at least in part on the patient data provided to the interpreter 202. In some implementations, the predictor 204 can be configured to generate a predicted visit note that predicts information that would be included in a subsequent visit note generated for the user (e.g. for the subject DPE). As indicated, such predicted information can include information relating to medical history, predicted symptoms, predicted treatment plans, predicted exam results, predicted discussions, etc. that are expected to be included in a subsequent visit note for the patient.

In some implementations, the predictor 204 can be configured to generate a predicted visit note that is formatted in accordance with one or more previous visit notes generated by a particular doctor. For instance, in implementations wherein the note prediction model 200 is trained on training data associated with a plurality of previous visit notes generated by the doctor (e.g. wherein the training is personalized towards the doctor), the predictor 204 can be trained to learn and predict a suitable formatting, stylization, grammar, etc. used by the doctor in generating such previous visit notes. The predictor 204 can then be trained to output predicted visit notes in accordance with such learned formatting, stylization, grammar, etc. In this manner, the predictor 204 can be trained to output predicted visit notes that include predicted information formatted and written in accordance with the doctor's previously generated visit notes.

The predicted visit notes can be output on a display of a user computing device associated with the doctor (e.g. user computing device 102 depicted in FIG. 1). The doctor or other suitable person can review the predicted visit note, and can make any desired changes or additions to the visit note through an interaction with the user device. In this manner, the predicted visit note can be presented as a baseline or template visit note associated with a subject DPE.

Figure 3:
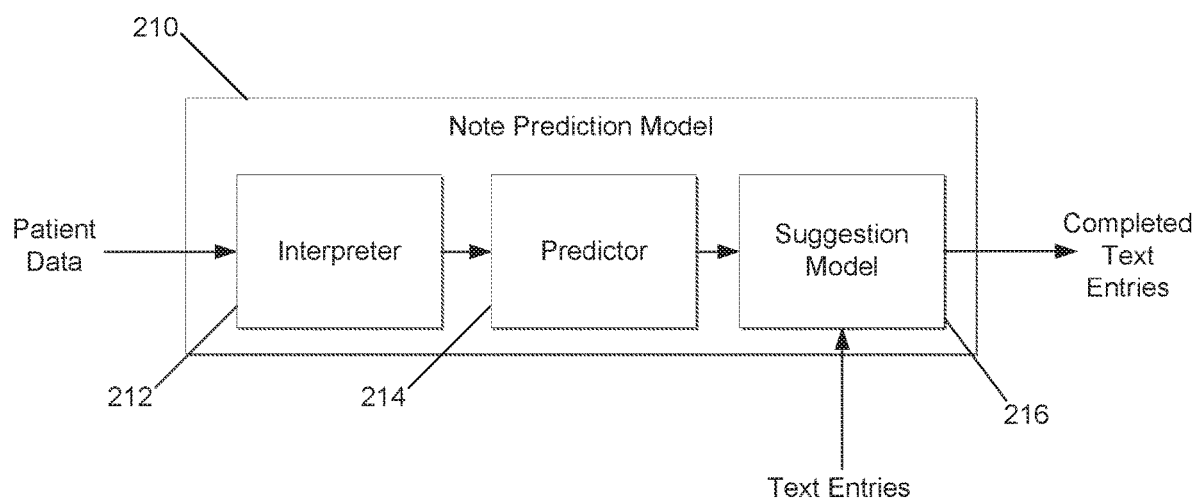

FIG. 3 depicts a block diagram of an example note prediction model 210 according to example embodiments of the present disclosure. The note prediction model 210 is similar to the prediction model 200 depicted in FIG. 2, except the model 210 includes a suggestion model 216. More particularly, the note prediction model 210 includes an interpreter 212 and a predictor 214. The interpreter 212 can be configured and trained to receive patient data associated with a patient as input and to provide one or more context vectors associated with the patient data as output. The predictor 214 can be configured and trained to receive the context vectors as input, and to generate one or more prediction vectors as output. The prediction vectors can be descriptive of information to potentially be included in a subsequent visit note associated with the patient. For instance, the prediction vectors can be descriptive of predicted information (e.g. medical history, predicted symptoms, predicted treatment plan, etc.) associated with the subsequent visit note.

The prediction vectors can be provided as input to the suggestion model 216. The suggestion model 216 can include one or more neural networks (e.g. deep neural networks). For instance, the suggestion model 216 can include one or more recurrent neural networks, such as for instance, LSTM recurrent neural networks, gated recurrent unit networks, or other suitable networks. In other implementations, in addition or alternatively to one or more neural networks, the suggestion model 216 of the note prediction model 210 can include other forms of machine-learned models such as, for example, support vector machines, hidden Markov models, and other machine-learned classifiers. In addition, in some implementations, the note prediction model 216 can include or implement additional alternative approaches such as rule-based systems (e.g., as machine-learned from data or manually created).

The suggestion model 216 can be configured to receive the prediction vectors from the predictor 214 as input. In some implementations, the suggestion model 216 can be configured to receive one or more text entries input by a user, for instance, through an interaction with the user computing device associated with the note prediction model 210. The text entries can include one or more characters, symbols, words, phrases, sentences, etc. For instance, the text entries can be incomplete words, sentences, phrases, etc. input by the user. In this manner, the text entries can be provided to the suggestion model 216 in real time or near real time as the user inputs the text entries. For instance, the text entries can be provided to the suggestion model 216 sequentially (e.g. on a character-by-character basis, word-by-word basis, etc.) as the user inputs the entries. As the suggestion model 216 receives the text entries, the suggestion model 216 can analyze the text entries in view of the prediction vectors to determine one or more suggested text entries based at least in part on the prediction vectors. More particularly, the one or more suggested text entries can be determined such that the suggested text entries can be used to complete the text entry provided by the user.

The one or more suggested text entries can be provided to the user, for instance, in the user interface with which the user is interacting (e.g. to input the text entries). The user can select a suggested text entry as desired to facilitate a determination of a completed text entry by the user computing device. For instance, the completed text entry can be a combination of the text entry input by the user and the selected suggested text entry. As another example, the completed text entry can be a new text entry determined based at least in part on the input text entry and the selected suggested text entry to capture the information included in the input and selected suggested text entries.

Figure 4:
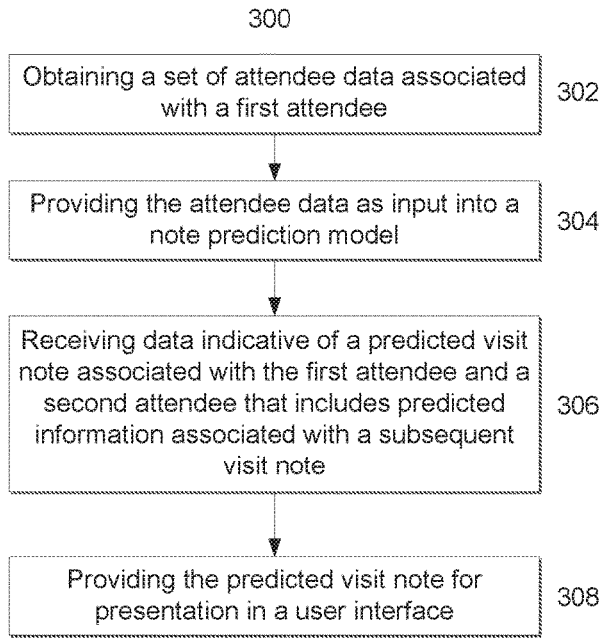
FIG. 4 depicts a flow diagram of an example method of predicting a visit note according to example embodiments of the present disclosure.

FIG. 4 depicts a flow diagram of an example method (300) of predicting visit notes according to example aspects of the present disclosure. Method (300) can be implemented by one or more computing devices, such as one or more of the computing devices depicted in FIG. 1. In addition, FIG. 4 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure.

At (302), the method (300) can include obtaining a set of attendee data associated with a first attendee of a subject encounter between the first attendee and a second attendee. For instance, the first attendee can be a patient associated with a DPE and the second attendee can be a doctor associated with the DPE. In such instances, the attendee data can include patient data associated with the patient. The patient data can include data descriptive of one or more visit notes previously generated for the patient. Each visit note can be associated with a particular DPE between the patient and a doctor. In some implementations, the patient data can be arranged sequentially based at least in part on an order of generation of the visit notes. For instance, data descriptive of a first visit note generated at a first time can be arranged prior to data descriptive of a second visit note generated at a subsequent time relative to the first time. In some implementations, the patient data can further include data associated with a subject DPE between the patient and a doctor.

At (304), the method (300) can include providing the attendee data as input into a machine-learned note prediction model. For instance, a user computing device can input the set of patient data into a local machine-learned note prediction model. As another example, a user computing device can transmit patient data over a network to a server computing device, and the server computing device can input the patient data into a machine-learned note prediction model stored at the server computing device. In implementation wherein the note prediction model is stored at a server computing device, the patient data may be stored at the server computing device or other suitable location. For instance, data indicative of one or more visit notes may be stored at the server computing device and/or at a user computing device communicatively coupled to the server computing device.

In some implementations, providing the attendee data as input to the note prediction model can include providing a string of text for input into the note prediction model. For instance, patient data associated with a first visit note may be provided as a first string of text according to an order in which the first visit note is to be read. Patient data associated with a second visit note can then be provided to the note prediction model as a second string of text according to an order in which the second visit note is to be read. As indicated, the patient data can further be provided to the note prediction model according to an order in which the visit notes were generated. It will be appreciated that the patient data can be provided to the note prediction model in any suitable manner without deviating from the scope of the present disclosure.

In some implementations, other suitable data can be provided to the note prediction model as input. For instance, such other data can include data associated with a global set of visit notes associated with a plurality of patients, a set of doctor specific visit notes generated by the doctor involved in the DPE, other suitable structured or unstructured information associated with the plurality of patients and/or the doctor, or other data. In this manner, it will be appreciated that any suitable information can be provided as input to the note prediction model to generate a predicted visit note.

At (306), the method (300) can include receiving data indicative of a predicted visit note associated with the first attendee and the second attendee as output of the note-prediction model. The predicted visit note can include predicted information expected to be included in a subsequent visit note for the first attendee based at least in part on the input attendee data (e.g. the previous visit notes for the patient). In some implementations, the predicted visit note can include such predicted information in a format, stylization, grammar, etc. that is tailored to that used by the second attendee (e.g. the doctor). For instance, the predicted visit note can be generated based at least in part on one or more previous visit notes generated by the doctor for one or more patients. In this manner, the note prediction model can be trained on a suitable set of training to output a suitable prediction note. The training of the note prediction model will be discussed in greater detail with respect to FIG. 6.

At (308), the method (300) can include providing the predicted visit note for presentation in a user interface. For instance, the predicted visit note can be provided for display in a user interface of a user computing device associated with the second attendee. In this manner, the predicted visit note can be presented to the second attendee (or other suitable person) as a baseline or template visit note for a subject encounter between the first attendee and the second attendee. The second attendee can edit, rearrange, add to, etc. the presented predicted visit note as desired through one or more suitable interactions with the user computing device. Once the visit noted is acceptable to the second attendee, the finalized visit note can be stored, for instance as part of the first attendee's and/or the second attendee's records for future use.

Figure 5:
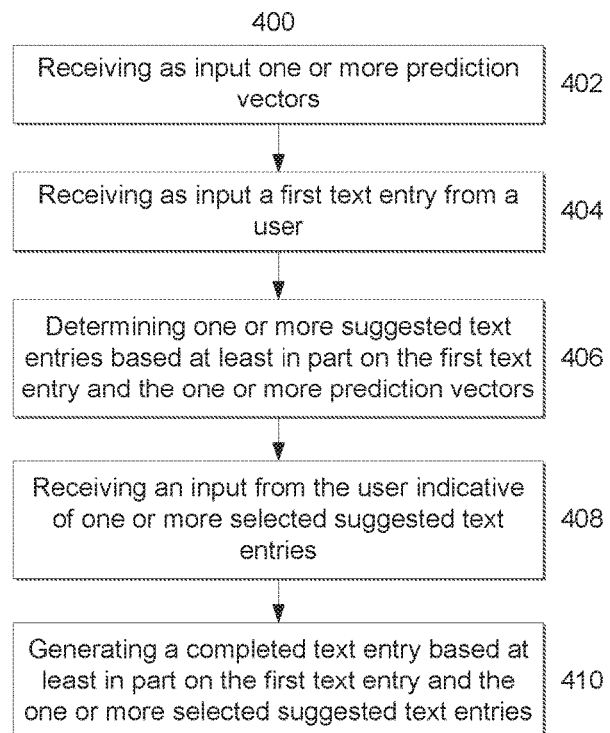
FIG. 5 depicts a flow diagram of an example method of generating a visit note according to example embodiments of the present disclosure.

FIG. 5 depicts a flow diagram of an example method (400) of generating visit notes according to example embodiments of the present disclosure. Method (300) can be implemented by one or more computing devices, such as one or more of the computing devices depicted in FIG. 1. In addition, FIG. 5 depicts steps performed in a particular order for purposes of illustration and discussion.

At (402), the method (400) can include receiving one or more prediction vectors as input by a machine-learned suggestion model in accordance with example aspects of the present disclosure. For instance, in some implementations, a predictor portion of the machine-learned note prediction model described with respect to FIG. 4 can generate one or more prediction vectors indicative of potential information that may be included within a predicted visit note. Each prediction vector can be descriptive of a subset of information to be potentially included in a predicted visit note.

At (404), the method (400) can include receiving data indicative of a first text entry input by a user of a user computing device. For instance, the user can input the first text entry through suitable interaction with the user computing device. The data indicative of the first text entry can be associated with a string of text, and can be received, for instance, in accordance with an order in which the text is input by the user. In this manner, the data indicative of the first text entry can be received in concurrently (or near concurrently) with the inputting of the text entry by the user.

At (406), the method (400) can include determining one or more suggested text entries based at least in part on the first text entry and the one or more prediction vectors. For instance, the suggested text entries can be text entries that can complete the first text entry to provide suitable information associated with the prediction vectors. In this manner, the suggested text entries can be determined to construct a grammatically, stylistically suitable, sentence, phrase, etc. that includes suitable information to be included in the predicted visit note. In this manner, such suggested text entries can be determined based at least in part on the patient data, one or more global visit notes, and one or more doctor specific visit notes.

At (408), the method (400) can include receiving data indicative of a user input associated with a selected suggested text entry. For instance, one or more suggested text entries can be presented to the user in a user interface associated with the user computing device. The presented suggested text entries can be interactive such that the user can select one or more of the suggested text entries to facilitate a construction of a completed text entry. In this manner, the selected suggested text entry can be a suggested text entry that was selected by the user.

At (410), the method (400) can include generating a completed text entry based at least in part on the first text entry and the one or more selected suggested text entries. For instance, a completed text entry can be a combination of the first text entry and a selected suggested text entry. In some implementations, the completed text entry can be a new text entry that captures the information included in the first text entry and the selected suggested text entry.

Figure 6:
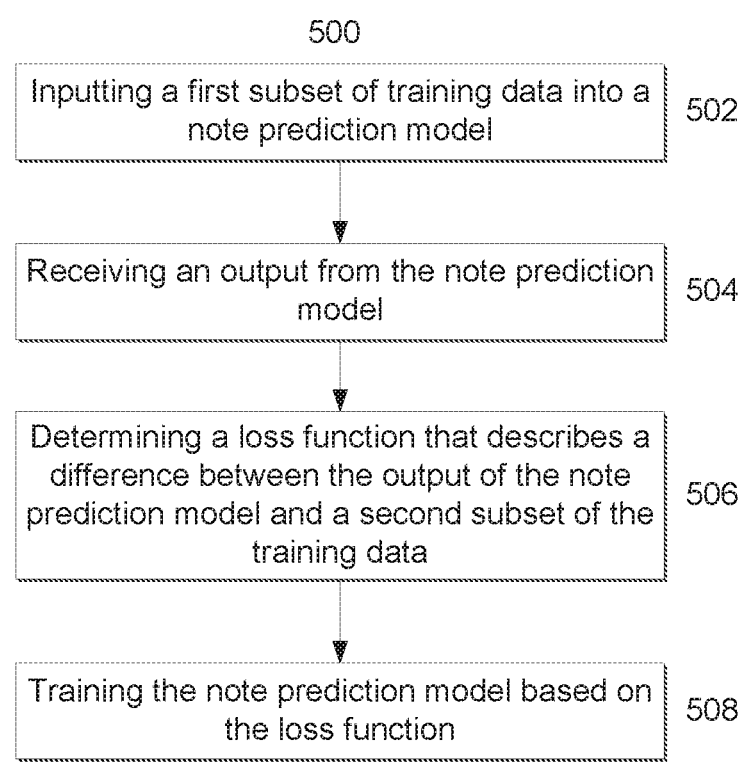
FIG. 6 depicts a flow diagram of an example method of training a note prediction model according to example embodiments of the present disclosure.

FIG. 6 depicts a flow diagram of an example method (500) of training a note prediction model according to example aspects of the present disclosure. Method (500) can be implemented by one or more computing devices, such as one or more of the computing devices depicted in FIG. 1. In addition, FIG. 6 depicts steps performed in a particular order for purposes of illustration and discussion.

At (502), the method (500) can include inputting a first subset of a set of training data into a note prediction model according to example aspects of the present disclosure. The training data can include data indicative of a plurality of global visit notes previously generated by any suitable number of doctors for any suitable number of patients. In some implementations the note prediction model can be personalized for a particular doctor. In such implementations, the training data can include data indicative of a plurality of doctor specific visit notes previously generated by the doctor for any suitable number of patients. It will be appreciated that various other suitable training data can be used without deviating from the scope of the present disclosure.

In this manner, the first subset of training data can include data indicative of one or more global visit notes and/or data indicative of one or more doctor specific visit notes. As indicated, the first subset of training data can be provided as one or more strings of text in accordance with an order in which the visit notes are to be read. Further, the first subset of training data can be provided in accordance with an order in which the visit notes were generated.

At (504), the method (500) can include receiving an output from the note prediction model. In some implementations, the output can include a predicted note. In some implementations, the output can include one or more prediction vectors.

In some implementations, the note prediction model can include various suitable portions (e.g. interpreter 202, predictor 204, suggestion model 216, etc.). In such implementations, the portions of note prediction model can be trained independently in portion-specific training sessions. For instance, the interpreter can be trained independently of a training of the predictor. In such implementations, the received output from the note prediction model can be an intermediate output generated by the particular portion associated with the training session. For instance, the received output can be one or more context vectors associated with the interpreter, a predicted visit note or one or more prediction vectors generated by the predictor, one or more suggested text entries generated by the suggestion model, etc.

At (506), the method (500) can include determining a loss function that describes a difference between the output of the note prediction model and a second subset of the training data. For instance, the second subset of training data can include a subsequent visit note relative to the visit notes included within the first subset of training data. The subsequent visit note can be a visit note generated by a particular patient and/or generated by a particular doctor. The subsequent visit note can be the visit note that the note prediction model aims to generate as a result of receiving the first subset of training data. In this manner, the loss function can describe a difference between a predicted visit note generated by the note prediction model and the subsequent visit note.

At (508), the method (500) can include training the note prediction model based at least in part on the loss function. For instance, training the note prediction model can include performing truncated backwards propagation through time to backpropagate the loss function through the note prediction model. A number of generalization techniques (e.g., weight decays, dropouts, etc.) can optionally be performed at 508 to improve the generalization capability of the models being trained. After the model has been trained at 508, it can be provided to and stored at a user computing device for use in predicting visit notes at the user computing device. More particularly, the training procedure described in 502-508 can be repeated several times (e.g., until an objective loss function no longer improves) to train the model.

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method of predicting documentation associated with an encounter between attendees, the method comprising:
   obtaining, by one or more computing devices, attendee data indicative of one or more previously generated visit notes associated with a first attendee of a subject encounter between the first attendee and a second attendee;
   inputting, by the one or more computing devices, the attendee data into a machine-learned note prediction model comprising a first neural network and a second neural network;

receiving, by the one or more computing devices, one or more context vectors as output of the first neural network;

inputting, by the one or more computing devices, the one or more context vectors into the second neural network of the machine-learned note prediction model;

receiving, by the one or more computing devices, one or more prediction vectors as output of the second neural network, the one or more prediction vectors being descriptive of information to potentially be included in a predicted visit note;

providing, by the one or more computing devices, the one or more prediction vectors as input to a suggestion model of the note prediction model;

providing, by the one or more computing devices, data indicative of a first text entry input by a user as input to the suggestion model; and receiving as output of the machine-learned note prediction model, by the one or more computing devices, data indicative of a predicted visit note, the predicted visit note comprising a set of predicted information expected to be included in a subsequently generated visit note associated with the first attendee, the set of predicted information comprising one or more suggested text entries determined based at least in part on the one or more prediction vectors and the data indicative of the first text entry.

2. The computer-implemented method of claim 1, wherein the attendee data comprises data indicative of one or more previously generated visit notes for the first attendee, each previously generated visit note being associated with a previous encounter of the first attendee.

3. The computer-implemented method of claim 1, wherein the attendee data further comprises data associated with the subject encounter between the first attendee and the second attendee.

4. The computer-implemented method of claim 3, wherein the data associated with the subject encounter comprises data provided to a user computing device prior to a generation of a visit note associated with the subject encounter.

5. The computer-implemented method of claim 1, wherein the first attendee is a patient associated with the subject encounter and the second attendee is a doctor associated the subject encounter, and wherein the attendee data includes data relating to a medical history of the patient.

6. The computer-implemented method of claim 5, wherein the predicted information comprises substantive information expected to be included in a subsequently generated visit note associated with the subject encounter based at least in part on the attendee data.

7. The computer-implemented method of claim 1, wherein the first neural network comprises a long short-term memory recurrent neural network.

8. The computer-implemented method of claim 1, wherein receiving, by the one or more computing devices, data indicative of a predicted visit note comprises receiving the data indicative of the predicted visit note as an output of the second neural network.

9. The computer-implemented method of claim 1, further comprising training, by the one or more computing devices, the note prediction model based on a set of training data; wherein training, by the one or more computing devices, the note prediction model comprises backpropagating, by the one or more computing devices, a loss function through the note prediction model.

10. The computer-implemented method of claim 9, wherein the training data comprises data indicative of a plurality of global visit notes.

11. The computer-implemented method of claim 9, wherein the training data comprises data indicative of a plurality of doctor specific visit notes.

12. A computing system, comprising:
one or more processors; and
one or more memory devices, the one or more memory devices storing computer-readable instructions that when executed by the one or more processors cause the one or more processors to perform operations, the operations comprising:
obtaining attendee data indicative of one or more previous visit notes associated with a first attendee of a subject encounter between the first attendee and a second attendee;
inputting the attendee data into a machine-learned note prediction model comprising a first neural network and a second neural network;
receiving, by the one or more computing devices, one or more context vectors as output of the first neural network;
inputting, by the one or more computing devices, the one or more context vectors into the second neural network of the machine-learned note prediction model;
receiving, by the one or more computing devices, one or more prediction vectors as output of the second neural network, the one or more prediction vectors being descriptive of information to potentially be included in a predicted visit note;
providing, by the one or more computing devices, the one or more prediction vectors as input to a suggestion model of the note prediction model;
providing, by the one or more computing devices, data indicative of a first text entry input by a user as input to the suggestion model; and
receiving, as output of the machine-learned note prediction model, data indicative of a predicted visit note, the predicted visit note comprising a set of predicted information expected to be included in a subsequently generated visit note associated with the subject encounter, the set of predicted information comprising one or more suggested text entries determined based at least in part on the one or more prediction vectors and the data indicative of the first text entry.

13. The computing system of claim 12, wherein the attendee data comprises data indicative of one or more previously generated visit notes for the first attendee, each previously generated visit note being associated with a previous encounter of the first attendee.

14. One or more tangible, non-transitory computer-readable media storing computer-readable instructions that when executed by one or more processors cause the one or more processors to perform operations, the operations comprising
obtaining patient data indicative of one or more previous visit notes associated with a patient;
inputting the patient data into a first neural network associated with a machine-learned note prediction model;
receiving one or more context vectors as output of the first neural network;
inputting the one or more context vectors into a second neural network associated with the machine-learned note prediction model;
receiving one or more prediction vectors as output of the second neural network, the one or more prediction vectors being descriptive of information to potentially be included in a predicted visit note;

providing the one or more prediction vectors as input to a suggestion model associated with the note prediction model;

providing data indicative of a first text entry input by a user as input to the suggestion model; and receiving data indicative of a predicted visit note, the predicted visit note comprising a set of predicted information expected to be included in a subsequently generated visit note associated with the patient, the set of predicted information comprising one or more suggested text entries determined based at least in part on the one or more prediction vectors and the data indicative of the first text entry.

* * * * *